United States Patent [19]

Birum et al.

[11] 4,179,483

[45] Dec. 18, 1979

[54] 2-CHLOROETHYL PHOSPHONATES

[75] Inventors: Gail H. Birum, Kirkwood; Richard F. Jansen, St. Louis, both of Mo.

[73] Assignee: Monsanto Company, St. Louis, Mo.

[21] Appl. No.: 945,669

[22] Filed: Sep. 25, 1978

Related U.S. Application Data

[63] Continuation-in-part of Ser. No. 855,533, Nov. 28, 1977, abandoned, which is a continuation-in-part of Ser. No. 831,707, Sep. 9, 1977, abandoned.

[51] Int. Cl.$^2$ .......................... C07F 9/40; C08N 5/53
[52] U.S. Cl. .................................. 260/941; 260/45.7 P
[58] Field of Search .............................. 521/106, 107; 260/45.7 P, 45.85, 941, 969; 560/8

[56] References Cited

U.S. PATENT DOCUMENTS

| | | | |
|---|---|---|---|
| 2,631,162 | 3/1953 | Ladd et al. | 260/946 |
| 2,877,260 | 3/1959 | Campbell et al. | 260/977 |
| 3,005,000 | 10/1961 | Cooper | 260/977 |
| 3,196,190 | 7/1965 | Nischk et al. | 260/941 |
| 3,779,956 | 12/1973 | Morehouse | 260/2.5 AJ |
| 3,781,388 | 12/1973 | Jenkner et al. | 260/953 |
| 3,801,542 | 4/1974 | Toy et al. | 260/45.85 R |

OTHER PUBLICATIONS

Komkov et al., "Chem. Abs.", vol. 53, (1959), 9035h.
Pudovik et al., "Reviews Uspekhi Khimii," May, 1968, pp. 317–332.
Kabachnik et al., "Chem. Abs.", (1948), 7241f.

*Primary Examiner*—Anton H. Sutto
*Attorney, Agent, or Firm*—Scott J. Meyer; James W. Williams, Jr.

[57] ABSTRACT

The present invention relates to 2-chloroalkyl (2-chloroalkyloxy)hydrocarbylphosphinylpropionates and a process for the preparation thereof. The invention also includes combinations of the said 2-chloroalkyl (2-chloroalkyloxy)hydrocarbylphosphinylpropionates with organic polymer substrates, such as polyurethanes and polyesters, in order to impart enhanced fire-retardancy to such otherwise flammable substrates.

3 Claims, No Drawings

2-CHLOROETHYL PHOSPHONATES

CROSS-REFERENCE TO RELATED APPLICATION

This is a continuation-in-part of application Ser. No. 855,533, filed Nov. 28, 1977, which in turn is a continuation of application Ser. No. 831,707, filed Sept. 9, 1977, both abandoned.

BACKGROUND OF THE INVENTION

1. Field of the Invention

The present invention relates to 2-chloroalkyl (2-chloroalkyloxy)hydrocarbylphosphinylpropionates, a process for the preparation thereof and flame retardant compositions comprising organic polymers together with the said 2-chloroaklyl (2-chloroalkyloxy)hydrocarbylphosphinylpropionates.

2. Description of the Prior Art

Certain phosphorus esters such as phosphate esters have been employed as flame retardant additives but have suffered from the defect of low-molecular weight and loss by volatilization from the substrate polymeric materials in which the phosphates were employed. For example, the addition of such phosphates to a polyurethane foam resulted in loss of some of the phosphates when the foams were heat aged, with consequent reduction of fire-retardancy.

SUMMARY OF THE INVENTION

It has now been found that certain 2-chloroalkyl (2-chloroalkyloxy)hydrocarbylphosphinylpropionate esters are particularly useful as flame retardants for organic polymeric materials. The invention includes combinations of the present 2-chloroalkyl (2-chloroalkyloxy)hydrocarbylphosphinylpropionates together with organic polymers such as polyurethanes, polyamides and polyesters.

The general method for the preparation of the 2-chloroalkyl (2-chloroalkyloxy)hydrocarbylphosphinylpropionates of this invention comprises step-wise treatment of a dichlorohydrocarbylphosphine with an epoxide (ethylene oxide or propylene oxide), and then with acrylic or methacrylic acids according to the following general equation.

$$RPCl_2 + 2CH_2\overset{O}{-\!\!\!-\!\!\!-}CHR' + CH_2=\underset{R'}{\overset{|}{C}}CO_2H \longrightarrow$$

$$R'CHClCH_2O\overset{O}{\underset{|}{\overset{\|}{P}}}CH_2\overset{}{\underset{R'}{\overset{|}{C}}H}\overset{O}{\overset{\|}{C}}OCH_2CHClR'$$

where
R is phenyl, methyl, or ethyl, and
R' is hydrogen or methyl.

An example where R is methyl and R' is hydrogen is shown by the preparation of 2-chloroethyl 3-[(2-chloroethoxy)methylphosphinyl]propionate from dichloro(methyl) phosphine, ethylene oxide, and acrylic acid.

$$CH_3PCl_2 + 2CH_2\overset{O}{-\!\!\!-\!\!\!-}CH_2 + CH_2=CHCO_2H \longrightarrow$$

$$ClCH_2CH_2O\overset{O}{\underset{|}{\overset{\|}{P}}}CH_2CH_2\overset{O}{\overset{\|}{C}}OCH_2CH_2Cl$$
$$\phantom{ClCH_2CH_2O}CH_3$$

Since the ring structure of propylene oxide may open in either of two ways when used in the present process, the product may contain either or both of the following two 2-chloropropoxy groups:

$$-OCH_2CHClCH_3 \text{ and } -OCH\overset{CH_2Cl}{\underset{CH_3}{\diagdown}}$$

Although it is generally preferred to carry out the reactions of the present invention without the use of a solvent, inert solvents may be used, for example, methylene chloride, 1,2-dichloroethane, toluene, chlorobenzene, and o-dichlorobenzene.

The temperature of the first step, the reaction of the dichlorohydrocarbylphosphine with the epoxide, may be in the range of about −20° C. to 125° C., the preferred range being 0° to 50° C.

The second step, the reaction of acrylic or methacrylic acid with the intermediate phosphorus ester of the first step, may be carried out at about 20° C. to 150° C., or preferably from about 50° C. to 150° C., the preferred temperature in each case depending on the specific reactants being used.

Stoichiometric amounts of the dichlorohydrocarbylphosphine and epoxide, that is, enough epoxide to react with all of the chlorine bonded to phosphorus, are generally used in the first step, but the process can be carried out with an excess over the theoretical proportions of either reactant. The epoxide is usually added to stirred and cooled dichlorohydrocarbylphosphine, preferably in the presence of a catalyst. Preferred catalysts are active hydrogen compounds including acids, such as mineral acids, e.g. hydrochloric acid (hydrogen chloride), sulfuric acid or phosphoric acid. Other active hydrogen compounds preferred as catalysts are acid generating compounds such as ethanol or ethylene chlorohydrin.

Further refining of the phosphorus ester intermediate product of step 1 is unnecessary, and the addition of acrylic or methacrylic acid can usually be started in the same reaction vessel as soon as the temperature has been adjusted to the desired level for the second step. A stoichiometric amount of the acrylic acid is preferred, based upon the amount of trivalent phosphorus ester produced in step 1, but larger amounts, e.g., 1 to 20 mole% excess, can be used. In some cases warming may be desirable after the addition of the acrylic acid to complete the reaction.

Stripping at elevated temperatures and/or reduced pressures may be used to remove small amounts of side reaction products. Standard procedures can be used to reduce acidity if needed, for example, washing with basic solutions or treatment with orthoformate esters or epoxides. For example, the product may be treated with aqueous sodium carbonate in order to neutralize any residual acidity. Another treatment which may be employed to carry the reaction to completion is an esterification treatment utilizing an esterifying agent such as triethyl orthoformate. Such after treatments, however, are not essential.

In the manufacture of flame retardant polymeric materials, the present invention therefore provides a method for enhancing the flame retardant characteristics of a substrate by the addition to such substrate at from 0.1 to 20 wt.% (preferably 1% to 10 wt.%) of the propionates of the present invention. The propionate may be added to the polymeric substrate, such as a polyester, by admixture with the molten or particulate form of the polymer, for example before extrusion into shaped articles such as films or fibers. The propionates may also be added as a component in the polymerization such as in the preparation of polyurethanes from polyol compounds and isocyanates.

DESCRIPTION OF THE PREFERRED EMBODIMENTS

The following examples illustrate specific embodiments of the present invention, but are not limitative of the scope of the invention.

EXAMPLE 1

Bis(2-chloroethyl)phenylphosphonite is prepared by the addition of 5.0 g of ethylenechlorohydrin and then 10.84 moles of gaseous ethylene oxide to 5.42 moles of dichloro(phenyl)phosphine with cooling at 16°–20° C. A 267 g. portion of this intermediate, containing 0.92 mole of bis(2-chloroethyl)phenylphosphonite, is stirred and cooled at 80°–85° C. as 66.3 g. (0.92 mole) of acrylic acid is added in 0.25 hr. The reaction mixture is warmed at 130°–135° C. for 3 hours and then stripped at reduced pressure, giving 300 g. of yellow liquid. A 159 g. portion is stirred in 125 ml. of chlorobenzene and 100 ml. of water as 10% sodium carbonate solution is added until the pH is 7.1. The organic layer is washed with water and then stripped at reduced pressure, giving 149.8 g. having a major $^{31}$P nmr peak at −43.5 ppm for 2-chloroethyl 3-[(2-chloroethoxy)phenylphosphinyl]propionate.

As another reaction of the invention, the treatment of 0.5 mole of dichloro(methyl)phosphine with 1.0 mole of ethylene oxide while being cooled at 0°–5° C., followed by the addition of 0.5 mole of acrylic acid and then warming to 130° C. gives 2-chloroethyl 3-[(2-chloroethoxy)methylphosphinyl]propionate.

EXAMPLE 2

Flame retardant compositions are produced with 10 wt.% of the propionates of Example 1 in nylon 66 and in polyethylene terephthalate.

What is claimed is:

1. 2-chloroalkyl (2-chloroalkoxy)hydrocarbylphosphinylpropionates of the general formula,

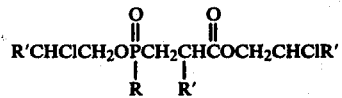

where R is phenyl, methyl or ethyl and R' is hydrogen or methyl.

2. 2-chloroethyl 3-[(2-chloroethoxy)phenylphosphinyl]propionate.

3. 2-chloroethyl 3-[(2-chloroethoxy)methylphosphinyl]propionate.

* * * * *